(12) United States Patent
Friedman

(10) Patent No.: US 9,423,409 B2
(45) Date of Patent: Aug. 23, 2016

(54) ARTICULATED SAMPLE CONTAINER RACK APPARATUS, RACK CONVEYOR SYSTEMS, AND METHODS OF CONVEYING SAMPLE CONTAINERS

(71) Applicant: Siemens Healthcare Diagnostics Inc., Tarrytown, NY (US)

(72) Inventor: Glenn Friedman, Redding, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/397,781

(22) PCT Filed: Apr. 29, 2013

(86) PCT No.: PCT/US2013/038670
§ 371 (c)(1),
(2) Date: Oct. 29, 2014

(87) PCT Pub. No.: WO2013/165911
PCT Pub. Date: Nov. 7, 2013

(65) Prior Publication Data
US 2015/0101911 A1    Apr. 16, 2015

Related U.S. Application Data

(60) Provisional application No. 61/640,075, filed on Apr. 30, 2012.

(51) Int. Cl.
*B65G 47/34* (2006.01)
*G01N 35/04* (2006.01)
(Continued)

(52) U.S. Cl.
CPC . *G01N 35/04* (2013.01); *B01L 9/06* (2013.01); *B65G 17/12* (2013.01);
(Continued)

(58) Field of Classification Search
CPC ........... B65G 2201/0261; B65G 17/32; B65G 17/12; B65G 17/002; G01N 35/04; B65D 21/0204; A47F 7/0028; A47B 81/007
USPC ............. 198/867.11, 867.13, 803.14; 422/65; 220/23.4, 23.8, 23.86; 206/446, 558; 211/71.01, 74, 77
See application file for complete search history.

(56) References Cited

U.S. PATENT DOCUMENTS 3,310,151 A     3/1967    Carter
3,348,658 A    10/1967    Cannon
(Continued)

FOREIGN PATENT DOCUMENTS

EP    0414644 A2    2/1991
EP    0 977 038 A2    2/2000
(Continued)

OTHER PUBLICATIONS

PCT International Search Report and Written Opinion dated Sep. 27, 2013 (9 Pages).
(Continued)

*Primary Examiner* — James R Bidwell

(57) ABSTRACT

An articulated sample rack apparatus is disclosed. In one aspect, the articulated sample rack apparatus has a plurality of coupled rack components wherein at least some of the rack components have a receptacle having a bottom to receive a sample container, the rack having free ends and at least one hinge allowing articulation between at least some of the rack components. Conveyor systems and methods to convey sample racks are provided, as are other aspects.

24 Claims, 12 Drawing Sheets

(51) Int. Cl.
*A47F 7/28* (2006.01)
*B01L 9/06* (2006.01)
*B65G 17/12* (2006.01)

(52) U.S. Cl.
CPC ..... *B01L 2200/025* (2013.01); *B01L 2200/028* (2013.01); *G01N 2035/0413* (2013.01); *G01N 2035/0486* (2013.01)

(56) References Cited

U.S. PATENT DOCUMENTS

| | | | |
|---|---|---|---|
| 3,521,785 A | 7/1970 | Bergmann et al. | |
| 3,538,962 A | 11/1970 | Gilson | |
| 3,788,450 A | 1/1974 | Tschunt et al. | |
| 4,944,924 A * | 7/1990 | Mawhirt | G01N 35/021 206/446 |
| 5,137,693 A * | 8/1992 | Mawhirt | B01L 9/06 206/446 |
| 5,651,941 A * | 7/1997 | Stark | B01L 9/06 220/676 |
| 6,266,948 B1 | 7/2001 | Serra | |
| 2006/0286619 A1 | 12/2006 | Ricci et al. | |

FOREIGN PATENT DOCUMENTS

| | | |
|---|---|---|
| JP | H01 158356 A | 6/1989 |
| WO | 03/065048 A1 | 8/2003 |

OTHER PUBLICATIONS

Supplementary EP Search Report dated Nov. 20, 2015 of corresponding European Application No. 13784608.5, 5 Pages.

* cited by examiner

ARTICULATED SAMPLE CONTAINER RACK APPARATUS, RACK CONVEYOR SYSTEMS, AND METHODS OF CONVEYING SAMPLE CONTAINERS

RELATED APPLICATIONS

The present application claims priority to U.S. Provisional Patent Application No. 61/640,075 filed Apr. 30, 2012, and entitled "ARTICULATED SAMPLE CONTAINER RACK APPARATUS, RACK CONVEYOR SYSTEMS, AND METHODS OF CONVEYING SAMPLE CONTAINERS," the disclosure of which is hereby incorporated herein by reference in its entirety for all purposes.

FIELD

The present invention relates generally to sample container racks, and systems and methods adapted for conveying sample containers between locations.

BACKGROUND

Testing within clinical laboratories, for example, may involve measuring one or more chemical constituents in a biological fluid obtained from a patient, such as whole blood, blood serum, blood plasma, spinal fluid, interstitial fluid, urine, or the like. Automated clinical analyzers, automated immunoassay equipment, and other automated processing equipment (e.g., centrifuges and pre-processing equipment) may be used to reduce the number of trained technicians required to perform analyses or pre-analysis processing, improve overall accuracy, and reduce the cost per operation performed.

Typically, such automated clinical analyzers or automated equipment may include an automated track system that is adapted to automatically transfer sample containers (e.g., sample tubes) from one location to another). In some embodiments, rigid sample racks containing multiple sample containers (e.g., multiple sample tubes) may be conveyed by the automated track system. In other embodiments, individual sample tube carriers (referred to herein as "sample tube pucks") each including a single sample container may be conveyed on an automated track system, and possibly diverted to one or more additional tracks for processing or analysis.

Conveying sample containers in rigid sample racks has advantages in terms of throughput. However, such sample racks may be difficult to convey within the tight space envelope desired for analyzers and processing equipment. In particular, turning tight corners in order to reverse a conveying direction may be problematic. Similarly, conveying individual sample containers in pucks may be problematic because they are spaced apart and, thus, may provide lower throughput. Accordingly, improved sample container conveyor systems and methods are sought after.

SUMMARY

According to a first aspect, an articulated sample container rack apparatus is provided. The sample container rack apparatus includes a plurality of coupled rack components, at least some of the coupled rack components having a receptacle configured and adapted to receive a sample container, the receptacle including a bottom, the plurality of coupled rack components having first and second free ends, and at least one hinge allowing relative rotation between at least some of the rack components.

According to another aspect, an articulated sample container rack apparatus is provided. The sample container rack apparatus includes a plurality of rack components having a total number of between 3 and 10, at least some of the rack components having a receptacle adapted to receive a sample container, wherein the receptacle includes a sidewall and a bottom, link sets connected to the rack components at first and second vertically-spaced locations, and retainers coupled to each of the rack components to restrain vertical motion of the link sets relative to the rack components and yet allow rotation of the rack components relative to the link sets.

According to another aspect, a sample container rack conveyor system is provided. The sample container rack conveyor system includes a track formed between a first wall and a second wall, at least one of the walls comprising a moveable wall having cleats extending into the track, and an articulated sample container rack adapted to be moved along the track by the moveable wall, the articulated sample container rack having a plurality of coupled rack components, at least some of the coupled rack components having a receptacle adapted to receive a sample container, the plurality of coupled rack components having first and second free ends, and at least one hinge allowing articulation between at least some of the coupled rack components.

In another aspect, a method of conveying a sample container rack is provided. The method includes providing an articulated sample container rack, the articulated sample container rack having a plurality of coupled rack components, at least some of the coupled rack components having a receptacle adapted to receive a sample container, the plurality of coupled rack components having first and second free ends, and at least one hinge allowing relative articulation between at least some of the rack components, and moving the flexible sample container rack along a track with a moveable wall.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

BRIEF DESCRIPTION OF THE DRAWINGS

The invention will be better understood by referring to the detailed description taken in conjunction with the following drawings.

DETAILED DESCRIPTION

In view of the foregoing difficulties, there is an unmet need to reduce the space needed for transferring sample containers and/or allow more system flexibility for transferring sample containers within sample container conveyor systems.

Accordingly, in one embodiment, an articulated sample container rack apparatus is provided that allows sample containers to be conveyed in relatively small groups. The articulated sample container rack apparatus includes a plurality of coupled rack components including at least one hinge allowing articulation between at least some of the rack components. At least some of the rack components have a receptacle (e.g., recess) configured and adapted to receive a sample container such as a sample tube. The sample tube may contain a biological fluid to be processed and/or tested at a testing and/or processing station. The rack components have a receptacle including a bottom configured to contact the sample container, and may include a holder having one or more locator fingers configured and operational to locate the sample container within the rack component.

In another embodiment, a sample container rack conveyor system is described. The sample rack conveyor system includes a track having first and second walls and a floor, the track being configured and adapted to receive the articulated sample container racks. At least one of the walls comprises a moveable wall. The moveable wall may have cleats extending into the track that engage spaces between the rack components. An articulated sample container rack having a plurality of coupled rack components and one or more hinges allowing articulation between at least some of the coupled rack components may be conveyed by the cleats on the moveable wall. Additional embodiments wherein the conveyor system includes a secondary moveable wall are disclosed, which can be used to spin the rack components so that a barcode on the sample container may be read.

These and other aspects and features of embodiments of the invention will be described with reference to FIGS. 1A-7 herein.

Figure 1A:
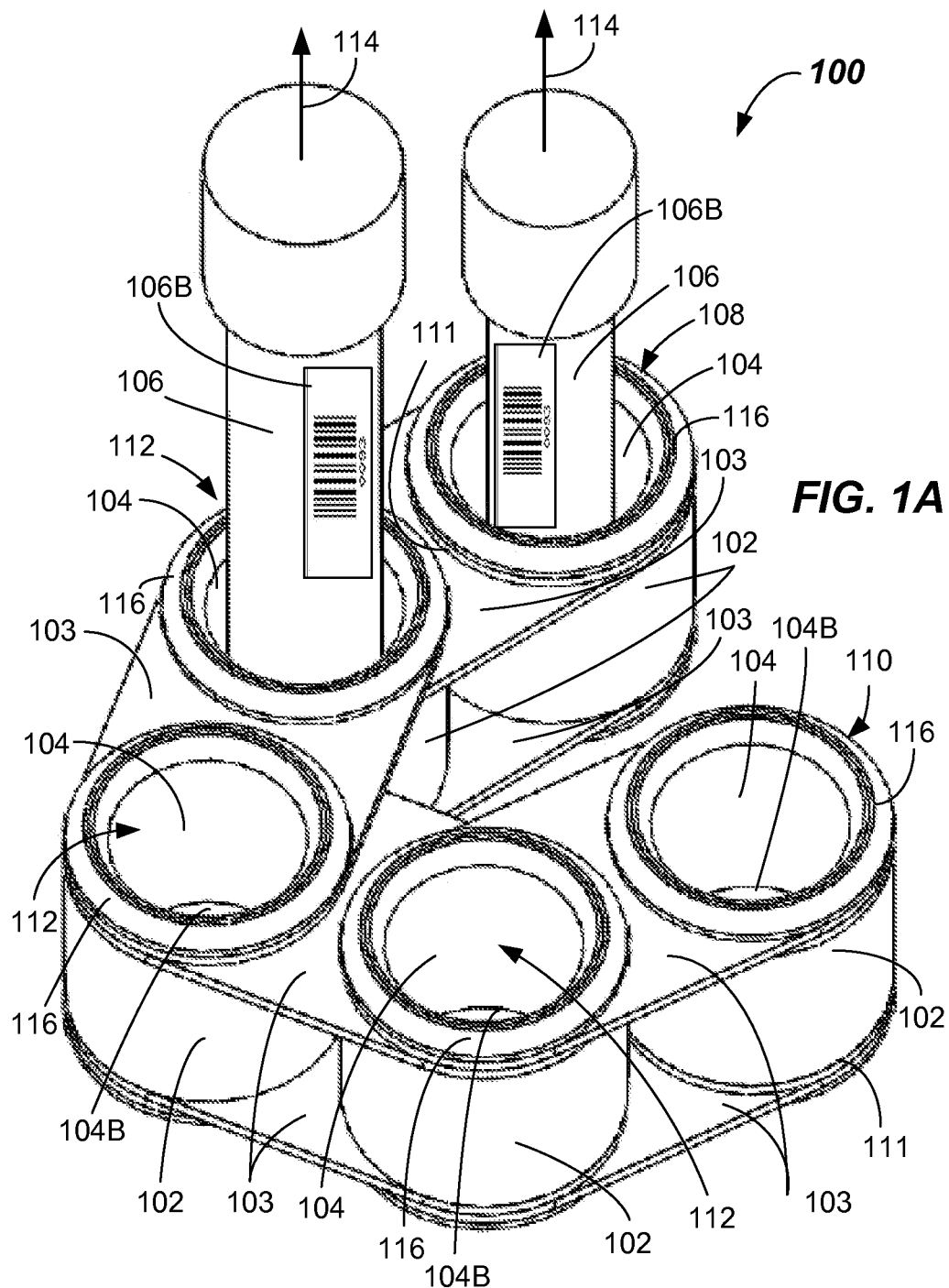
FIG. 1A illustrates an isometric view of an articulated sample container rack apparatus according to embodiments.

Referring now to FIG. 1A, an example embodiment of an articulated sample container rack apparatus 100 is illustrated. The articulated sample container rack apparatus 100 will be referred to as "articulated sample container rack apparatus," or "articulated sample container rack," or "sample container rack," or "sample rack," or just "rack" herein. The sample container rack 100 includes a plurality of rack components 102 that are coupled to one another by a plurality of links 103. In particular, as shown, a plurality of links 103 are rotationally coupled to each of the rack components 102. The rack components 102 may be generally cylindrical in shape and may be identical to one another in some embodiments. The rack components 102 may be made of a suitable plastic material, such as a thermoplastic. For example, Polyoxymethylene (POM), also known as acetal, polyacetal, and polyformaldehyde, is an engineering thermoplastic that may be used. Optionally, Nylon may be used. Other materials may be used. The rack components 102 may have a diameter of about 27 mm or greater and height of about 35 mm or greater, for example. Other dimensions may be used. The links 103 may be generally flat in shape and may be identical to one another in some embodiments. The links 103 may be made of a rigid material, such as steel, and may be about 1.5 mm thick, for example. The links 103 may have a center-to-center dimension of greater than about 28 mm, or even between about 28 mm and about 35 mm in some embodiments. The center-to-center dimension of the links 103 may be selected so that adjacent rack components 102 may be spaced at less than about 5 mm from one another. Other materials, thicknesses, and center-to-center dimensions may be used.

At least some of the rack components 102 have a receptacle 104 with a sidewall and a bottom 104B that is configured and adapted to receive a sample container 106 therein. The bottom 104B is configured and adapted to contact a bottom of the sample container 106 or a holder that receives the sample container 106. For example, in some embodiments, the bottom 104B may be part of a sample container holder 105 (see FIG. 1B) that may be received in the receptacle 104 so that the sample container 106 is held in a generally upright configuration and is generally centered within the rack component 102. The sample container 106 may be a capped or uncapped sample-containing tube. Other types of sample containers 106 may be received in the receptacles 104. However, the sample rack 100 may be adapted for carrying 12 mm to 16 mm biological liquid sample tubes.

The sample container rack 100 has a first free end 108 and a second free end 110. The term "free end" means that an end one of the rack components 102 is coupled to only one other adjacent rack component 102. Washer-shaped spacers 111 may be provided at the free ends 108, 110 to enhance commonality of components used in the rack 100. Center rack components 102 are attached to two adjacent rack components 102. At least some of the rack components 102 include a hinge 112 (e.g., a pivot axis) allowing articulation (e.g., relative rotation) between at least some of the rack components 102. In the depicted embodiment, all of the rack components 102 that include a receptacle 104 may have the ability to rotate substantially freely (e.g., 360 degrees or more), with minimal friction, about a rotational axis 114 (hinge axis) generally aligned with a center of the sample container 106 as shown in FIG. 1A. In this manner, the sample container rack 100 may be conveyed on a conveyor system 120 (See FIG. 1B) and, at one or more locations on the conveyor system 120, each of the rack components 102 may be spun and a barcode 106B on one, a subset, or all of the sample containers 106 in the sample container rack 100 may be read by a barcode reader. In the depicted embodiment, at least one of the hinges 112, and preferably all of the hinges 112 are substantially aligned with a location of a receptacle 104. Retainers 116 may be coupled to each of the rack components 102. A retainer 116 (only a few labeled) may be provided adjacent to each link 103 or spacer 111 to restrain the links 103 from vertical motion relative to the rack components 102. Retainers 116 may be threaded rings, for example.

Figure 1B:
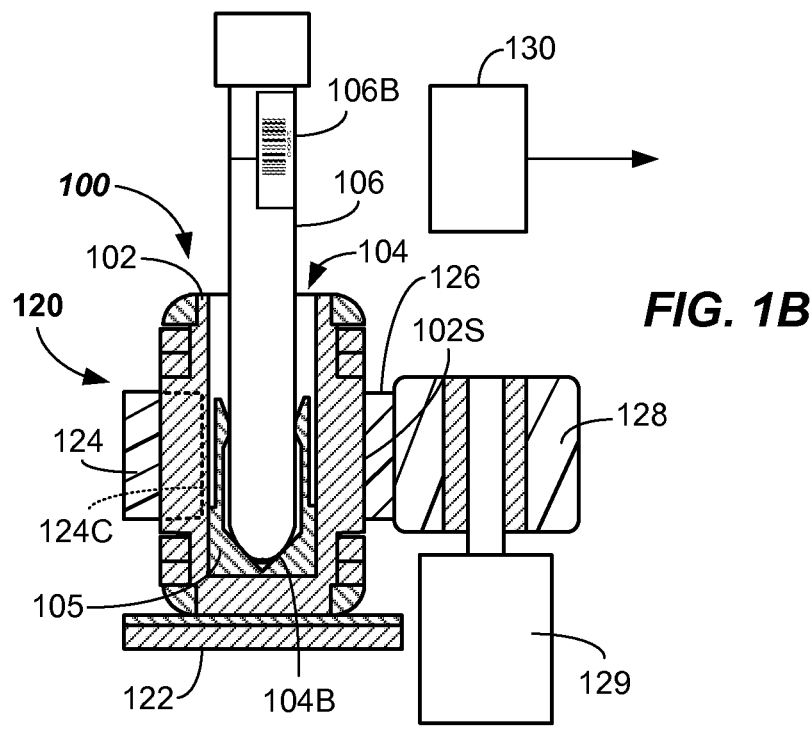
FIG. 1B illustrates a cross-sectioned side view of a portion of a rack conveyor system for an articulated sample container rack apparatus including two moveable walls according to embodiments.

The conveyor system 120 in the depicted embodiment of FIG. 1B includes a track having a stationary floor 122 upon which the sample container rack 100 may slide, and at least one moveable wall 124. The stationary floor 122 of the track may be made of a low friction material, or include a low friction surface treatment or layer (e.g., a Teflon layer). Suitable low friction materials include Nylon, High Density Polyethylene (HDPE), or the like. Other low friction materials may be used. The conveyor system 120 may also include additional moveable walls and/or stationary walls (See FIGS. 5A-6). In the depicted embodiment, a secondary moveable wall 126 may be provided, and the rack 100 is received between the moveable wall 124 and the secondary moveable wall 126. Portions of the track may be formed by the stationary floor 122, the moveable wall 124, and the secondary wall 126, wherein at least one of the walls comprises a moveable wall.

The secondary moveable wall 126 may be provided at least locally, such as in the area shown where a barcode 106B on the sample container 106 may be read. The barcodes 106B may be read by spinning each rack component 102 by contacting a side surface 102S of the rack component 102 with the secondary moveable wall 126. The secondary moveable wall 126 may be a compliant high-friction material, such as an elastomer such as natural rubber, polyurethane, or the like. The material should have a relatively high coefficient of friction Cf1. The surface may be roughened or a low slip coating may be added to achieve a high coefficient of friction Cf1. The secondary moveable wall 126 may be moved by any suitable means. For example, a moveable member 128, which may be a rotating wheel or other suitable article for causing rotation of the secondary moveable wall 126, may be used. Other support members (e.g., idler wheels) may be used along the secondary moveable wall 126. The moveable member 128 may be rotated by any suitable motive device 129, such as a variable speed motor, or the like.

To cause rotation of the rack component 102 in contact with the moveable walls 124, 126, the secondary moveable wall 126 may be operated (e.g., moved) at a rate different than the moveable wall 124. A rate that is faster than, slower than, or even reversed or stopped relative to the moveable wall 124 will cause rotation (spinning) of the rack components 102 and sample containers 106 received therein. In particular, a slight interference may be provided so that the walls 124, 126 slightly pinch the rack components 102.

In operation, cleats 124C (shown dotted in FIG. 1B) of the moveable wall 124 are adapted to extend into the track and contact at least some of the rack components 102 and move the rack 100 along the stationary floor 122 of the track. The cleats 124C on the moveable wall 124 hold the rack components in a defined moving position, and the relatively faster or slower secondary moveable wall 126 may cause rotation of the rack components 102. In one or more embodiments, the material of the moveable wall 124 may have a relatively lower coefficient of friction Cf2 than that of the secondary moveable wall 126, i.e., Cf2<Cf1. This will increase slippage of the side surface 102S of the rack component 102 on the moveable wall 124, but minimize slippage on secondary moveable wall 126. The moveable wall 124 may be a compliant material, such as an elastomer (e.g., silicone, fluorosilicone, polyurethane, or the like.) In some embodiments, a rougher surface texture may be used on the secondary moveable wall 126 to achieve the relatively lower coefficient of friction Cf2 of moveable wall 124. Accordingly, in operation, as the rack 100 is moved along, the relative rate difference between the moveable wall 124 and secondary moveable wall 126 spins the rack components 102 positioned between the walls 124, 126, and the barcode 106B may be read by a barcode reader 130 as the rack 100 passes by. In this manner, the barcode 106B may be read regardless of the rotational orientation of the barcode 106B in the sample container rack 100. In an alternative embodiment, the moveable wall 124 may be stopped momentarily when a rack component 102 is positioned adjacent to the barcode reader 130 and the rack component 102 may be spun by the secondary moveable wall 126 in order to read the barcode 106B. Barcode reading stations such as those described above may be added at suitable locations in the conveyor system 120.

Figure 1C:
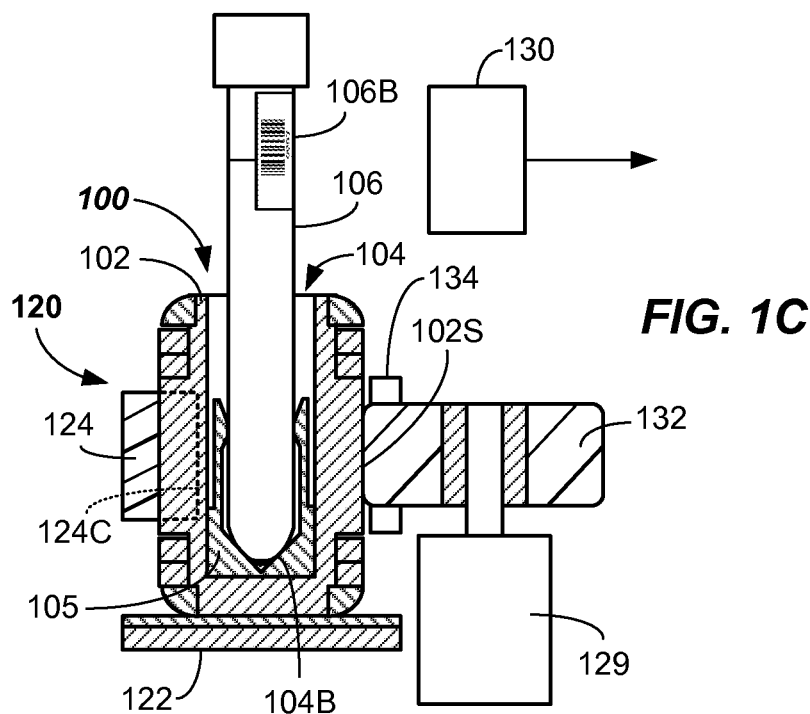
FIG. 1C illustrates a cross-sectioned side view of a portion of a rack conveyor system for an articulated sample container rack apparatus including one moveable wall according to embodiments.

In another embodiment shown in FIG. 1C, a moveable member 132 may extend through a stationary wall 134 of the conveyor system 120. The moveable member 132 may be a compliant wheel of a high-friction material such as those described above. The moveable wall 124 may be as previously described. As the sample rack 100 is moved along, the moveable member 132 spins the rack component 102 positioned adjacent to the moveable member 132 and the barcode 106B may be read by the barcode reader 130. Again, in this manner, the barcode 106B may be read regardless of the rotational position of the barcode 106B in the rack 100.

Figure 2A:
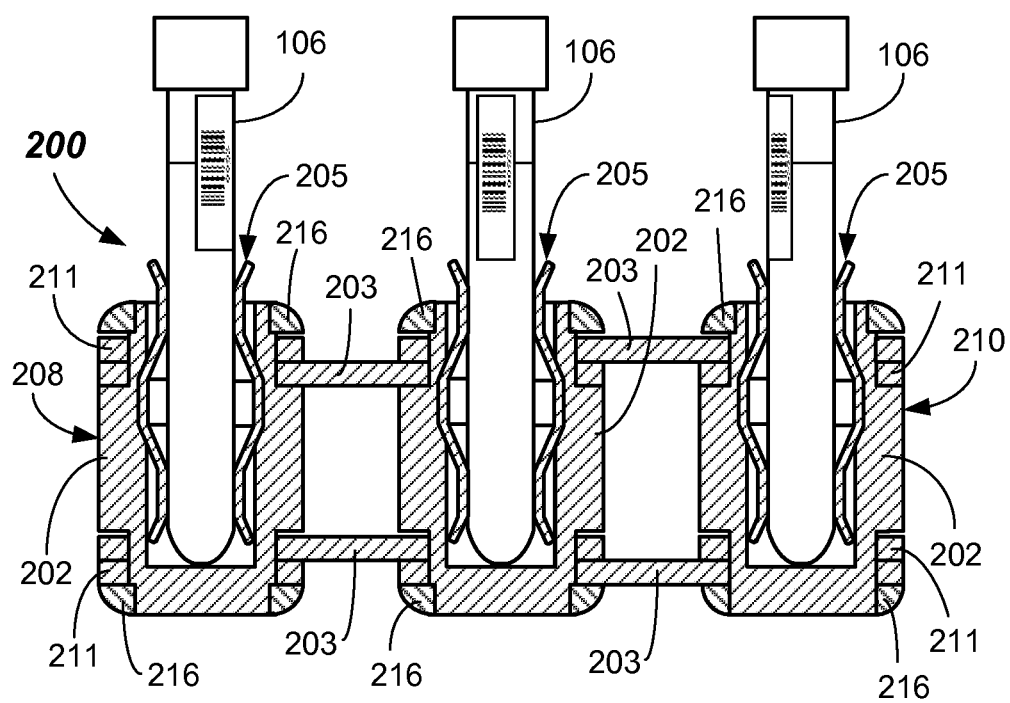
FIG. 2A illustrates a cross-sectioned side view of an alternative articulated sample container rack apparatus according to embodiments.
Figure 2B:
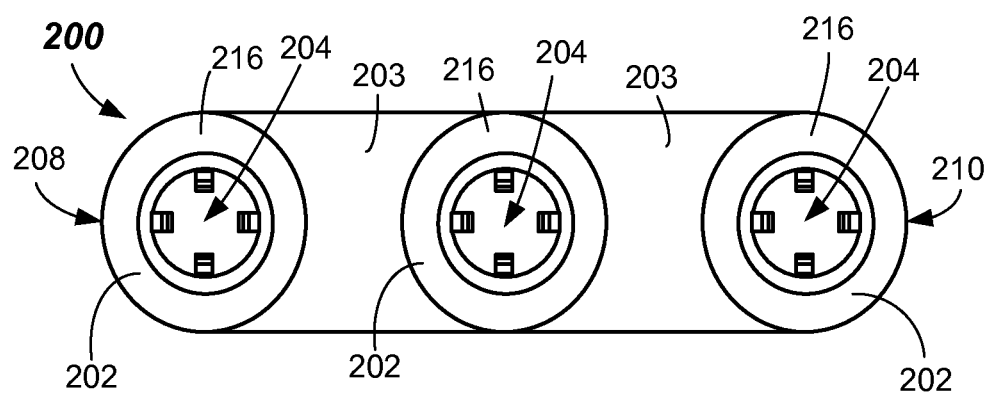
FIG. 2B illustrates a top view of an alternative articulated sample container rack apparatus according to embodiments.
Figure 2C:
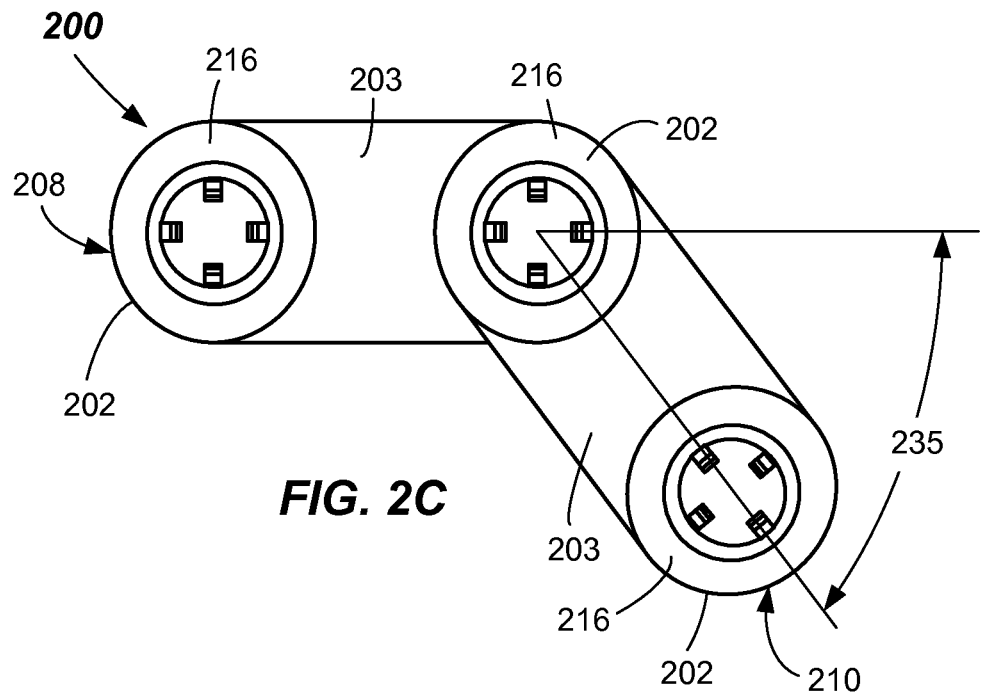
FIG. 2C illustrates a top view of an alternative articulated sample container rack apparatus shown misaligned according to embodiments.

Now referring to FIG. 2A-2C, an alternative articulated sample container rack 200 is shown. In the depicted embodiment, sample rack 200 has three rack components 202. However, it should be understood that a number of rack components 202 between the first and second free ends 208, 210 in the sample rack 200 may be 15 or less in one or more embodiments, between 3 and about 10, or even between 3 and about 7 in some embodiments. Each of the rack components 202 may be individually rotatable by 360 degrees or more. As in the previous embodiment, a plurality of links 203 may be coupled to each of the rack components 202 near a top and bottom thereof. Washer-shaped spacers 211 may be used on the ends 208, 210 so that the rack components 202 may have a common configuration. Thus, each end rack component of the rack components 202 may have multiple end links 203 and spacers 211 coupled thereto. Also, as shown, the rack apparatus 200 comprises multiple retainers 216 coupled to each of the rack components 202. The retainers 216 may be coupled to the rack components 202 and may function to restrain vertical motion of the plurality of links 203 relative to the rack components 202, yet allow free rotation of the rack components 202 relative to the plurality of links 203. Suitable gaps may be provided to allow ease of rotation. The sample container rack 200 may include a sample container holder 205 in one or more of the receptacles 204, each having a plurality of leaf spring fingers adapted to grip the sides of the sample container 106 received therein. The sample container holder 205 may comprise stamped metal fingers that may be interconnected by a broken ring, for example. The stamped metal fingers may be coupled to the sides by the ring being compressed and snapped into a groove or grooves formed in the body of the rack components 202.

As shown in FIG. 2C, a degree of articulation capability of the rack apparatus 200 is illustrated. A component-to-component articulation angle 235 may be at least 15 degrees or more, at least 30 degrees or more, at least 45 degrees or more, at least 90 degrees or more, or even up to about 120 degrees in some embodiments. The degree of articulation possible is only limited by contact between the links 203 and the rack components 202. Because of the articulation capability, the rack apparatus 200 may turn very sharp corners, as will be apparent when viewing a conveyor system 520 (see FIGS. 5A-5B and 6) in which the rack 100 may be operated.

Figure 3:
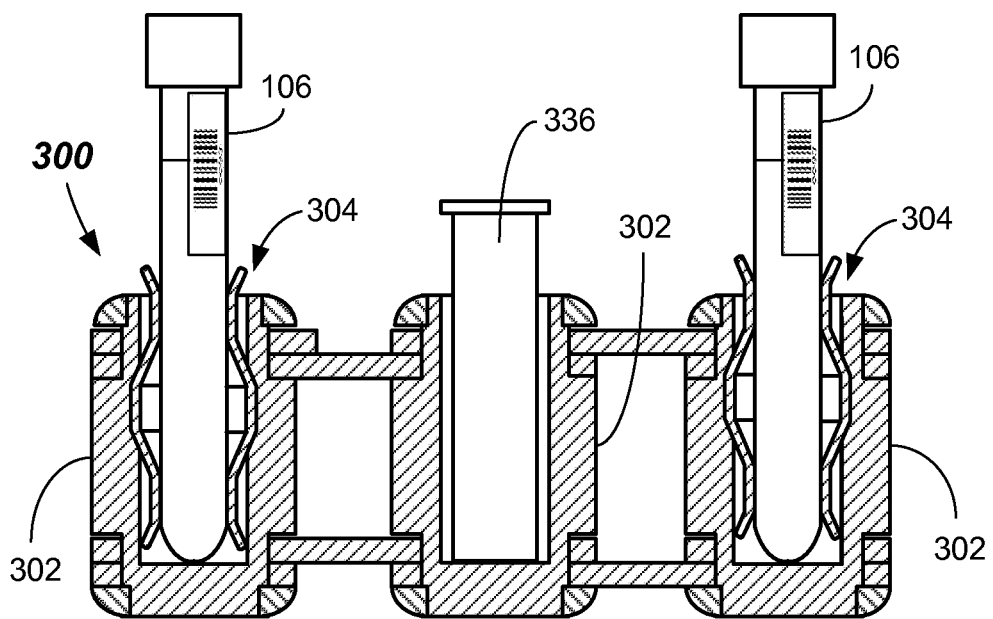
FIG. 3 illustrates a cross-sectioned view of another alternative articulated sample container rack apparatus including a center payload-carrying component according to embodiments.

Another embodiment of a sample container rack apparatus 300 is shown in FIG. 3. In this embodiment, less than all of the rack components 302 are configured and adapted to receive sample containers 106. For example, in the depicted embodiment, one or more of the center rack components 302 may be adapted to carry a payload, such as a reagent container 336 containing a reagent on the rack 300, while others may be adapted to receive sample containers 106 in receptacles 304 thereof. A reagent is a substance for use in a chemical reaction and especially for use in chemical synthesis and analysis. The rack 300 is otherwise constructed as previously described.

Figure 4A:
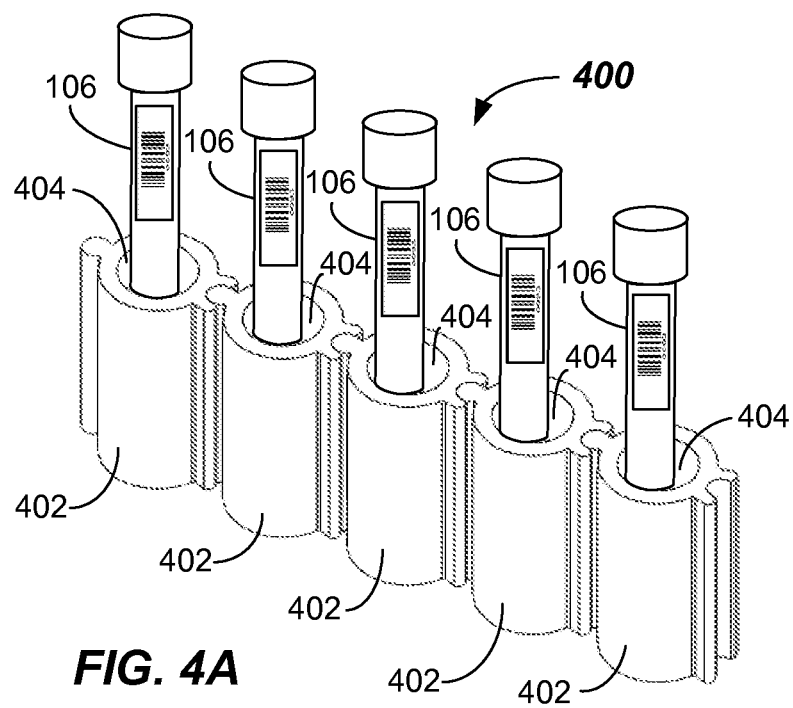
FIGS. 4A and 4B illustrate isometric views of another alternative articulated sample container rack apparatus according to embodiments (sample containers removed for clarity in FIG. 4B).
Figure 4B:
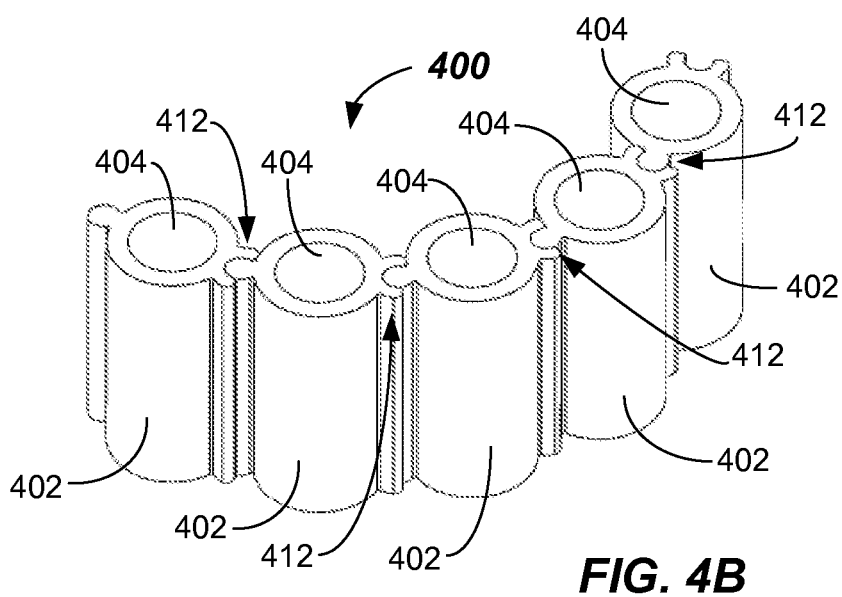

Another embodiment of a sample container rack apparatus 400 is shown in FIGS. 4A-4D. In this embodiment, a plurality of rack components 402 have receptacles 404 that are configured and adapted to receive sample containers 106, as was previously described. Each rack component 402 may include a sample container holder 405 as disclosed in FIG. 1B, for example. However, in the depicted embodiment, the rack components 402 are connected together by hinges 412, and at least one of the hinges 412, and preferably all of the hinges 412 are offset from a location of the receptacles 404. Any number of the rack components 402 may be hinged together to assemble the rack 400. Five rack components 402 are shown in FIGS. 4A-4B. However, this embodiment may include two (see FIG. 4D) or more, three or more, four or more, or even five or more rack components 402, and the like. In some embodiments, the rack 400 may include less than 15 rack components, or between 2 to about 10 rack components 402, or even between 3 to about 7 rack components 402. The hinge 412 may extend an entire height of the rack component 402 or less than all thereof.

Figure 4C:
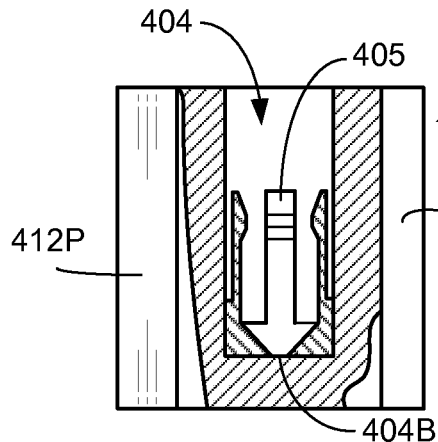
FIG. 4C illustrates a cross-sectioned side view of another alternative articulated sample container rack apparatus according to embodiments.
Figure 4F:
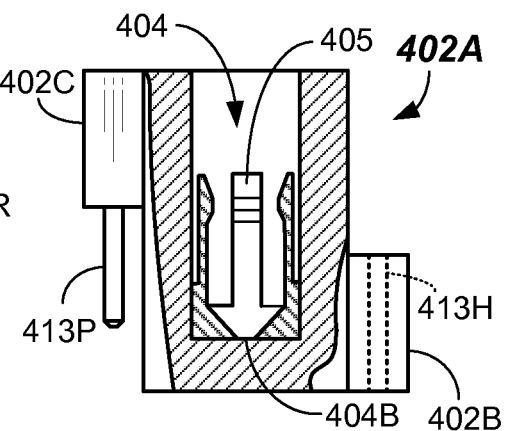
FIG. 4F illustrates a cross-sectioned side view of another alternative articulated sample container rack apparatus according to embodiments.
Figure 4D:
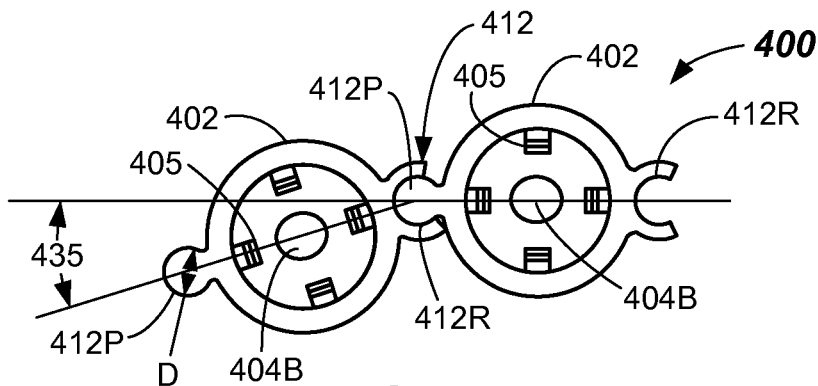
FIG. 4D illustrates a top view of another alternative articulated sample container rack apparatus shown misaligned according to embodiments.

As shown in FIGS. 4C and 4D, each one of the rack components 402 may include a receptacle 404 having a bottom 404B and a sample container holder 405 received therein. Only two linked components are shown in FIG. 4D. However, more than 2 and up to about 15 may be linked, for example. On one side, a recessed portion 412R may be provided, while on the other side a projecting portion 412P may be provided. Together, the recessed portion 412R and the projecting portion 412P engage to form the hinge 412. The projecting and recessed portions 412R, 412P each may include a circular profile on the mating portions thereof. A diameter D of the circular profile may be between about 5 mm and about 10 mm, for example. Other diameter values may be used. A slight gap between the recessed portion 412R and the projecting portion 412P may be provided to allow relatively free articulation. In this manner, two adjacent rack components 402 may be coupled together and provide articulation between them, allowing a capability of a component-to-component articulation angle 435 of greater than about 15 degrees, or even up to about 30 degrees, for example. One advantage of this embodiment is the ease by which any desired number of rack components 402 may be linked together. For example, the two shown in FIG. 4D may be assembled by sliding the projecting portion 412P into the recessed portion 412R from the top or bottom. The rack components 402 may be formed of a molded plastic, such as a thermoplastic material as discussed above. Other materials may be used.

Figure 4E:
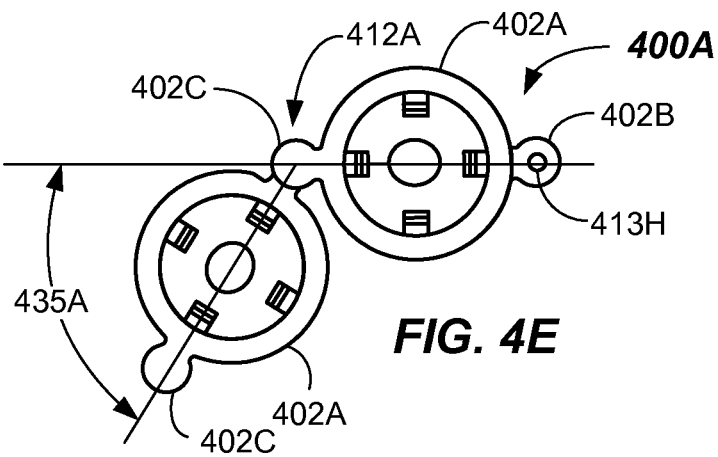
FIG. 4E illustrates a top view of another alternative articulated sample container rack apparatus shown misaligned according to embodiments.

FIGS. 4E and 4F illustrate another embodiment of a rack 400A and rack component 402A, respectively. In this embodiment, the articulation between the rack components 402A may be provided by a pin 413P received in a slightly larger hole 413H formed in a first boss 402B on an adjacent rack component 402A. The pin 413P may be coupled to (e.g., press fit, screwed, or glued) in a second boss 402C or may be integrally formed therewith. Because the hinge 412A is formed by a pin and hole, the only restraint on component-to-component articulation angle 435A is mechanical contact between adjacent rack components 402A. Thus, a component-to-component articulation angle 435A of greater than about 15 degrees, greater than about 30 degrees, or even up to about 60 degrees, may be provided, for example.

Figure 5A:
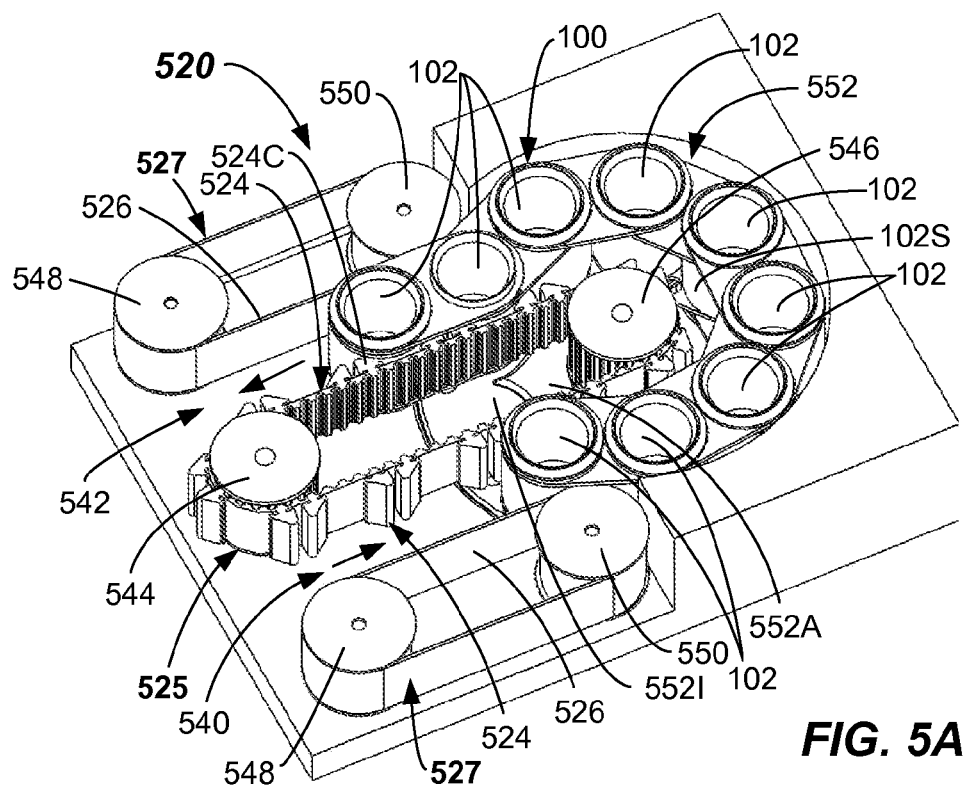
FIG. 5A illustrates a top isometric view of a portion of a sample container rack conveyor system according to embodiments.
Figure 5B:
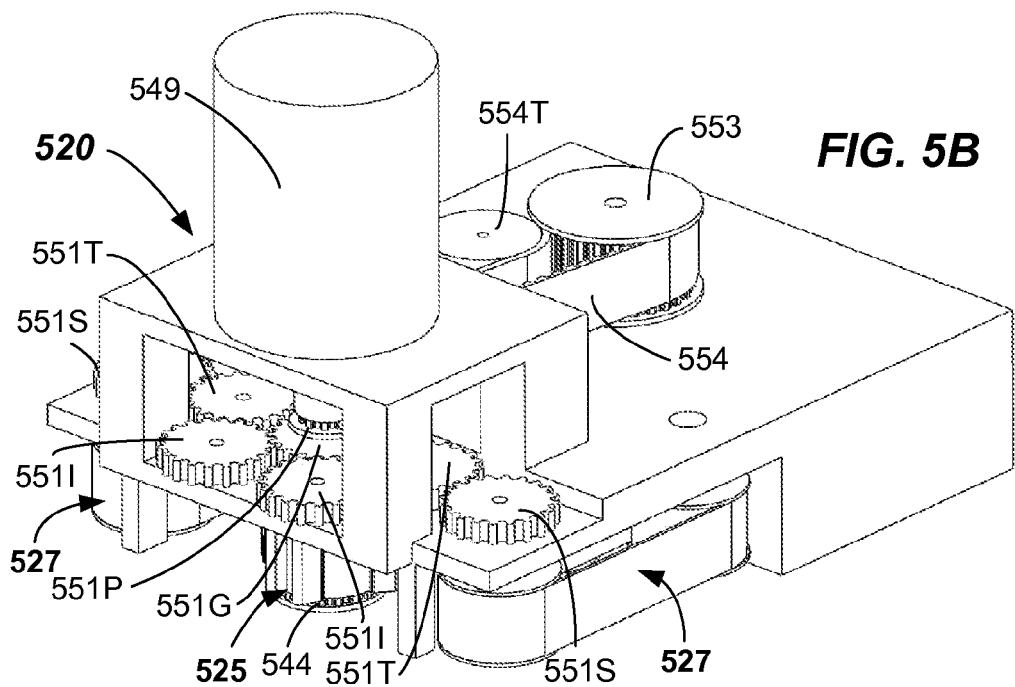
FIG. 5B illustrates an underside isometric view of a portion of a sample container rack conveyor system according to embodiments.
Figure 5C:
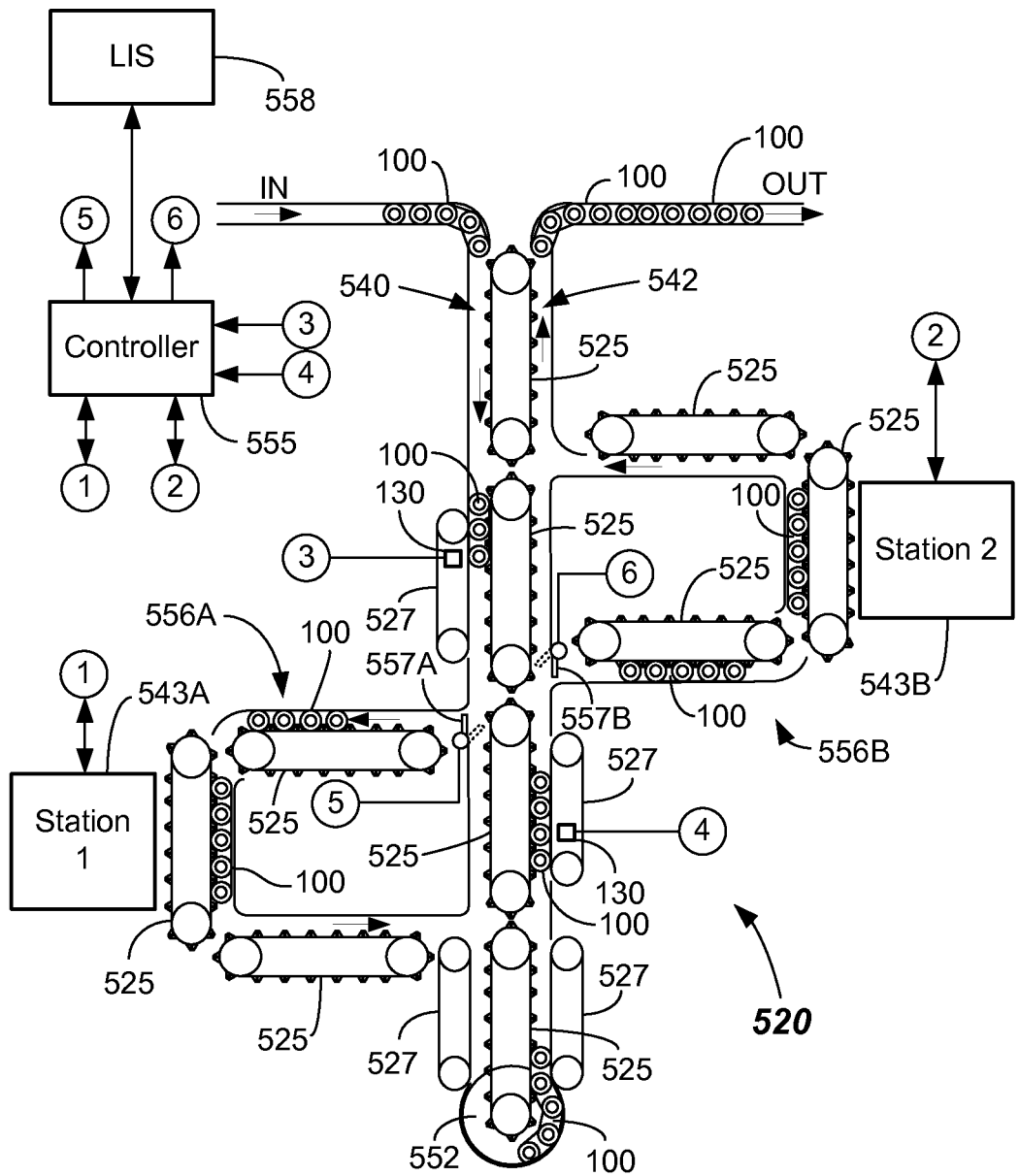
FIG. 5C illustrates a diagram of a sample container rack conveyor system according to embodiments.

An embodiment of a conveyor system 520 including one or more sample rack apparatus 100 is shown in FIGS. 5A-5C. The sample rack apparatus 100 as shown in FIG. 5A includes nine rack components. However, any number less than about 15 may be used. In some embodiments, between 3 and about 10 may be used, for example. Having the rack 100 include about 15 or less rack components 102 may be advantageous because it may allow for many like sample containers to be carried together to a destination by one rack 100, while being small enough to allow offshoots and diversions from a main track, including coordination thereof. Furthermore, having relatively smaller numbers of rack components, may allow release of sample container subgroups more quickly, because they do not need to wait for completion of tests ordered on a large number of sample containers. Also, there may be time limits for completion of some diagnostic tests, and use of a small number of rack components facilitates prompt completion, as the rack may only have to wait at a station until all the tests on the relatively small rack 100 are completed. Additionally, or alternatively, the use of a smaller number of rack components may leave spaces for reentry onto a main track without waiting, and may not require large buffer areas at a station. The conveyor system 520 may include a delivery track 540 and return track 542. The system 520 may deliver one or more sample racks 100 to one or more analysis and/or processing stations 543A, 543B for analysis and/or processing provided along the delivery track 540 and/or return track 542 or both. The system 520 as shown in FIG. 5C includes two stations 543A, 543B. However, it should be understood that any number of stations may be used. Stations 543A, 543B may include any type of analysis and/or processing equipment, such as diagnostic equipment, chemical analyzers, immunoassay systems, pre-processing or post-processing stations, storage stations, centrifuges, or the like. The stations 543A, 543B may include automated means for aspirating samples from the sample containers contained in the racks 100 or, optionally, the entire sample container may be transported into the analysis and/or processing equipment.

The system 520 further includes, as shown in FIG. 5A, at least one moveable wall 524 having a plurality of cleats 524C positioned along its length. However, it should be understood that the conveyor system 520 may include many moveable wall assemblies 525 and thus many such moveable walls 524 as shown in FIGS. 5A and 5C. The cleats 524C may be molded and integral with the moveable wall 524 or may be attached to the moveable wall 524 by suitable fastening means such as rivets or adhesive. The cleats 524C may be spaced at appropriate intervals along the moveable wall 524 such that one or more cleats 524C may be received between spaces between the rack components 102 of the rack 100. The inside of the moveable wall 524 may include serrations that mate with a drive pulley 544 and an idler pulley 546. The drive pulley 544 and idler pulley 546 may include cogs that mate with the serrations. Other suitable constructions may be used.

As shown in FIG. 5A, the moveable walls 524 may be formed as part of a moveable wall assembly 525 wherein the moveable walls 524 are formed on either side of an endless belt, as shown. As such, one moveable wall 524 is provided on the delivery track 540 and another is provided on the return track 542 and, because of their connectivity and orientation, each moveable wall 524 is driven in synchronism to move racks 100 in opposite directions along the delivery track 540 and the return track 542.

The system 520 may also include secondary moveable walls 526 spaced across one or more of the respective tracks 540, 542 from the moveable walls 524. The secondary moveable walls 526 may also be formed as part of a secondary moveable wall assembly 527 by an endless belt wound about a secondary drive pulley 548 and secondary idler pulley 550.

At the track corner there may be a turnaround from the delivery track 540 to the return track 542, and a turntable 552 (see also FIG. 5D) may be provided to aid in the direction change. The turntable 552 may include a rotatable disc 552A upon which one or more of the rack components 102 of the rack 100 may rest at various times. The turntable 552 may be rotated independent of the idler pulley 546 and the moveable wall 524. However, the turntable 552 may be driven by a same drive motor 549 (FIG. 5B). The turntable 552 may include indentations 552I (e.g., concave surface portions) that are of a size that they may locate and engage with the bottoms of the individual rack components 102 of the rack 100 thereon. While in the track corner, the turntable 552 is configured so that the cleats 524C disengage from the spaces between rack components 102 in the track corner, as shown in FIG. 5A, so that no contact between the cleats 524C and the sides 102S of the rack components 102 is made in the track corner, i.e., the rack components only reside on the turntable 552.

The various drive pulleys 544, 548 (FIG. 5A) may be driven by a suitable drive motor 549 (FIG. 5B). The drive pulley 544 may be driven at any speed desired for the conveyor system 500 by the main drive system. The main drive system may be driven at constant speed, variable speed, or may stop completely if desired. The secondary drive pulley 548 may be driven by the main drive system or may be driven by a secondary motive device 129 such as a drive motor shown in FIG. 1B. The secondary motive device 129 may be driven at the same or a different speed than the main drive motor. Thus, as described above, spinning of the rack components may be accomplished, such as in front of a barcode reader 130.

FIG. 5B illustrates an underside view of the conveyor system 520 and illustrates the main drive system thereof. In particular, the main drive system includes a drive motor 549 driving a primary drive pulley 551P. Primary drive pulley 551P drives driven pulley 553 via an endless belt 554. This driven pulley 553 is rigidly coupled to and rotates the turntable 552. A spring-biased tensioning pulley 554T may be used to maintain tension on the belt 554. Rigidly coupled to the primary drive pulley 551P or otherwise formed therewith is primary drive gear 551G. Also rigidly coupled to the primary drive pulley 551P is the drive pulley 544 of the moveable wall assembly 525. Accordingly, the moveable wall assembly 525 is driven directly by the drive motor 549. Primary drive gear 551G drives intermediate gears 551I, which in turn drives transfer gears 551T, which in turn drives the secondary gears 551S. Secondary gears 551S are directly coupled to and drive the secondary moveable wall assemblies 527.

Referring now to FIG. 5C, a high-level view of a conveyor system 520 configured and adapted to convey a plurality of articulated sample racks 100 is shown. Various sized sample racks 100 may be accommodated within the system 520, such as those having between 3 and 10 rack components. In some cases, a smaller number of rack components (e.g., 3 or less) may be used for STAT samples. The conveyor system 520 may include a plurality of moveable wall assemblies 525 that are configured and adapted to move the racks 100 about the system 520. Additionally, the system 520 may include one or more secondary moveable wall assemblies 527. Each of the secondary moveable wall assemblies 527 may be positioned to oppose a moveable wall assembly 525 across the respective tracks 540, 542. Positioned along one or more of the tracks 540, 542 may be one or more barcode readers 130. The barcode readers 130 may be provided at suitable locations to read the barcode labels 106B of the sample containers 106 carried by the racks 100 and interface with a controller 555 to map a location thereof and determine routing of the various racks 100 based upon test/process ordering information received from the Laboratory Information System (LIS) 558. The barcode readers 130 may be placed adjacent to and before at least some of the junctions where the racks 100 may depart from the delivery and return tracks 540, 542.

In the depicted embodiment, several station tracks 556A, 556B may be provided. The station tracks 556A, 556B may exit the delivery and/or return tracks 540, 542 and direct a rack 100 to a station 543A, 543B for processing and/or testing. In the depicted embodiment, station 1 543A and station 2 543B are provided. Any number of additional stations may be used. Also, one or more than one station may be provided on each station track 556A, 556B (see FIG. 6). The controller 555 may interface with an LIS 558 to determine the testing and/or processing to be performed on each sample, as well as to relay the results thereof. Once a rack 100 is loaded onto the system 500 either manually or by suitable automation onto the delivery track 540 at IN, the rack 100 is conveyed past the first barcode reader 130. As the rack 100 passes the barcode reader 130, each rack component 102 may be spun as described with reference to FIG. 1B (or FIG. 1C) and the barcode 106B may be read and communicated to the controller 555. If at least one of the sample containers 106 contained in the rack 100 has testing and/or processing ordered of the type being carried out at station 1 543A, then the rack 100 may be diverted to station 1 543A. The various wall assemblies 525 on the delivery and return tracks 540, 542 may all be moved in synchronism in some embodiments, whereas the motion of station tracks 556A, 556B may not be synchronized.

The diversion may be accomplished by actuating a gate 557A. Once diverted, the rack 100 may go directly to station 1 543A for processing and/or testing. Optionally, it may be held in a holding lane waiting for testing and/or processing at station 1 543A to be completed on all ordered samples. Once the processing and/or testing is completed for each of the sample containers 106 having an ordered test or process at station 1 543A, the results may be sent to the controller 555 and may be relayed to the LIS 558. Optionally, the results may be sent directly to the LIS 558 by the station 1 543A. The rack 100 may then be conveyed back onto the delivery lane 540. Because the various wall assemblies 525 on the delivery and return tracks 540, 542 are driven in synchronism, the system controller 555 always knows where any free spaces are, regardless of how complicated the layout is.

Figure 5D:
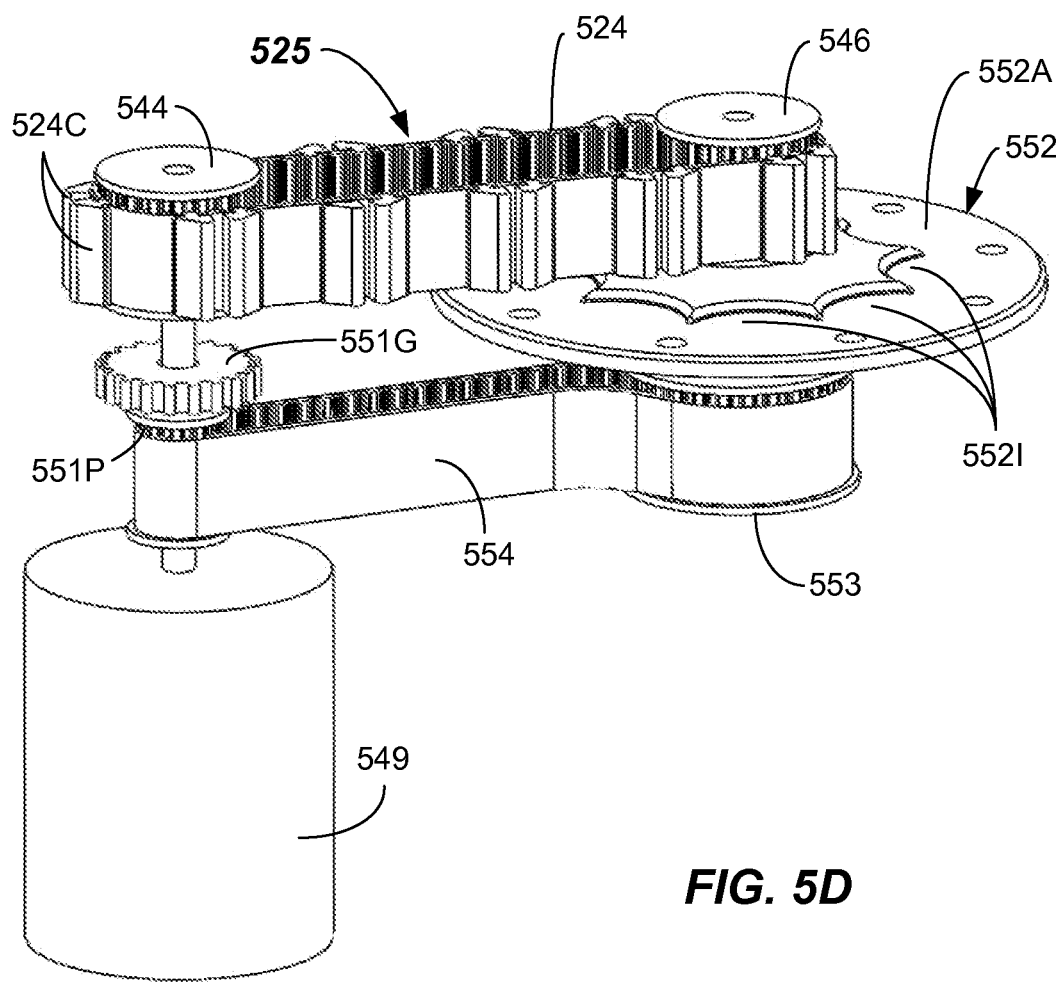
FIG. 5D illustrates an isometric view of some components of a sample container rack conveyor system according to embodiments.

Next, the rack 100 may encounter the turnaround which moves the rack 100 around the track corner on a turntable 552 and onto the return track 542 as was described with reference to FIGS. 5A and 5B. At the turnaround, the rack 100 may disengage the moveable wall 524 and may be carried on the turntable 552 through at least part of the excursion. As shown in FIG. 5D, indentations 552I of the approximate shape of the bottom of the rack components 102 aid in moving the rack 100 around the track corner. The turntable 552 moves the rack 100 in the track corner and the front of the rack 100 is again picked up by the cleats 542C of the moveable wall as the rack 100 enters onto the return track 542. Again, the rack 100 may encounter a barcode reader 130 and, again, the barcodes 106B on each sample container 106 may be read.

If at least one of the sample containers 106 contained in the rack 100 has testing and/or processing ordered of the type being carried out at station 2 543B, then the rack 100 may be diverted to station 2 543B. The diversion may be accomplished by actuating a gate 557B. Once diverted, the rack 100 may go directly to station 2 543B for processing and/or testing. Optionally, it may be held in a holding lane and await testing and/or processing on a previous rack 100 at station 2 543B to be completed. Once the processing and/or testing is completed for each of the sample containers 106 having an ordered test or process, the results may be sent to the controller 555 and may be relayed to the LIS 558. Optionally, the results may be sent directly to the LIS 558. The rack 100 may then be conveyed back onto the return lane 542 and conveyed out of the system 520 at OUT.

A suitable number of stations may be used in the system 520 to meet the expected demand including more than one station on each of the delivery and return tracks 540, 542. However, if the capacity of one or both stations is exceeded, then the conveyor system 520 may stop or there may be a rack return system provided. For example, the rack return system may be the same as the turnaround shown in FIG. 5A, so that any station may be bypassed one or more times until the desired station again has a capacity to hold or test or process the test sample. If a second turnaround is provided, then the IN and OUT lanes would be installed upstream and downstream of the second turnaround, respectively, and another gate would be added to divert the rack 100 to the OUT lane only if all tests and/or processing had been completed on all sample containers 106 in the rack 100 as determined by a barcode reader positioned upstream of the additional gate.

Figure 5E:
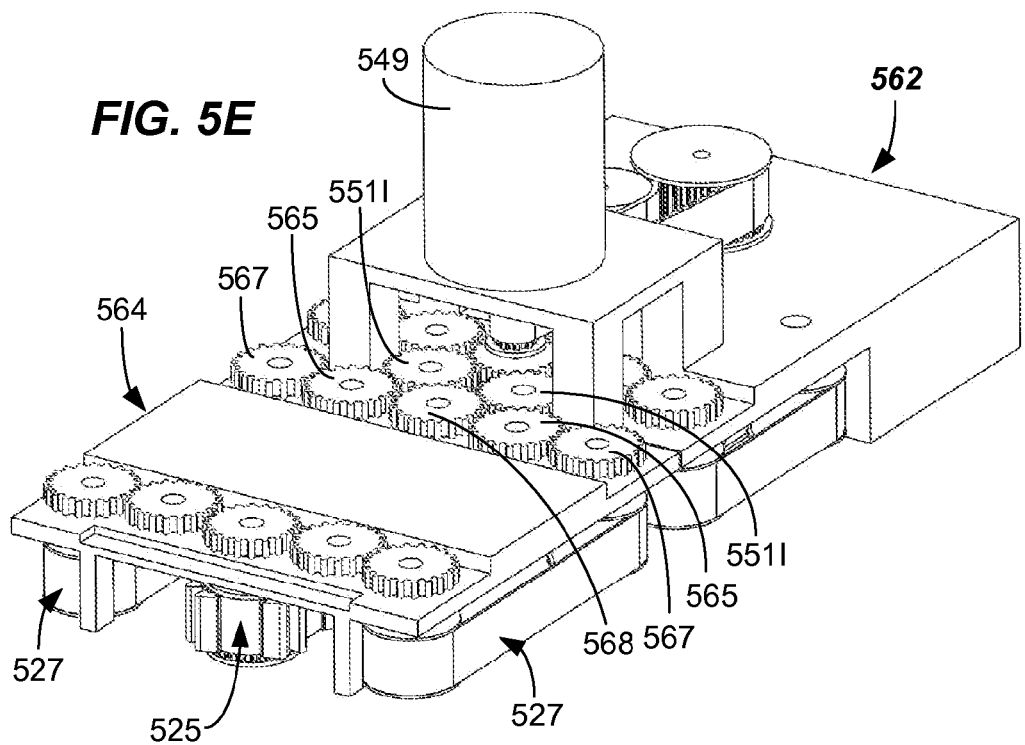
FIG. 5E illustrates an isometric underside view of segments of a conveyor system according to embodiments.
Figure 5F:
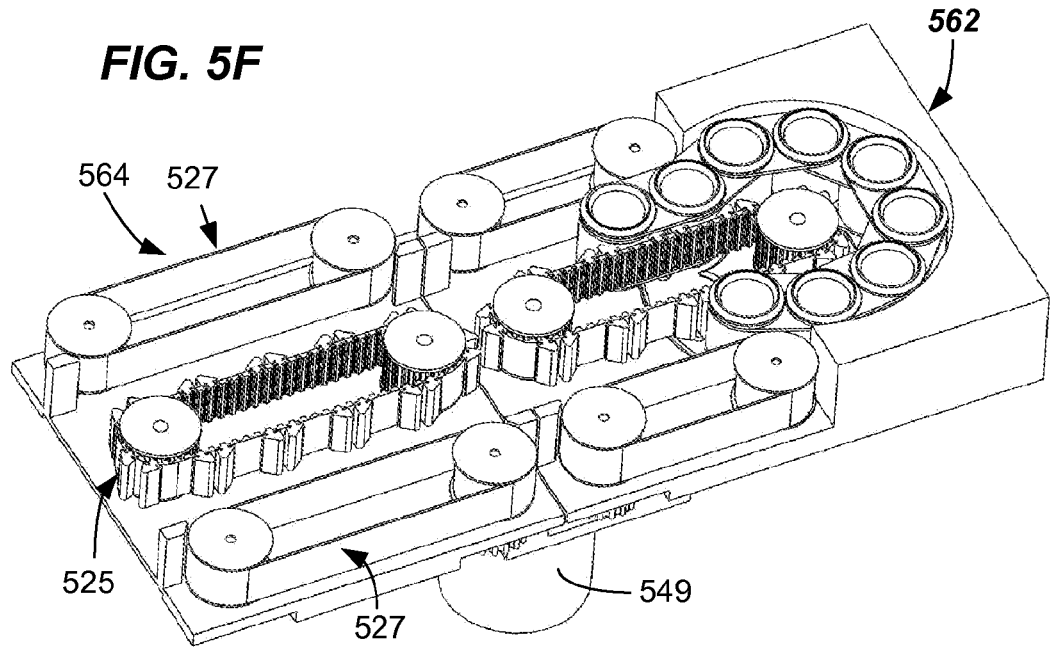
FIG. 5F illustrates an isometric top view of segments of a conveyor system according to embodiments.

As shown in FIGS. 5E and 5F, the drive system for the turnarounds may also be used to drive moving wall assemblies 525, 527 that are located in areas other than at the turnarounds. In the depicted embodiment, a turnaround section 562 and a straight section 564 are shown coupled. However, it should be apparent from the foregoing that multiple straight sections 564 may be driven by one drive motor 549. The drive motor 549 drives intermediate gears 551I that are coupled to transfer gears 565. Drive gears 567 of the secondary wall assemblies 527 are driven by transfer gears 565. The drive gear 568 of the moveable wall assembly 525 is driven by one or both of the intermediate gears 551I. Additional gears on the other end of the straight section may be coupled to the wall assemblies 525, 527 and used to drive another coupled section. The various gears may be common sizes and manufactured from any suitable plastic material (e.g., thermosetting plastics).

Figure 6:
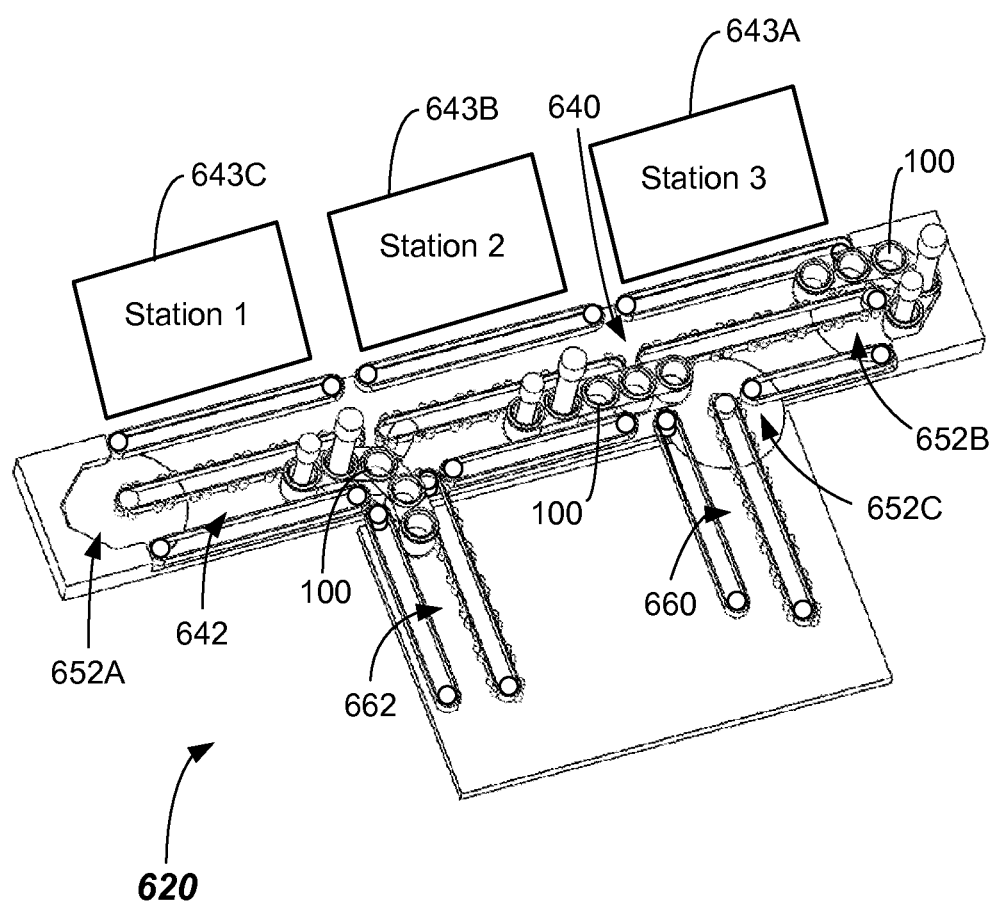
FIG. 6 illustrates an isometric view of another embodiment of a sample container rack conveyor system according to embodiments.

A construction of a conveyor system 620 is shown in FIG. 6. This conveyor system 620 includes delivery lane 640 and return lane 642. As shown, the system 620 includes the ability for racks 100 to be received in an inflow lane 660, circulate to one or more stations 643A-643C, and be diverted to an outflow lane 662 by a moveable gate when all the desired testing and/or processing on sample containers in the rack 100 is completed. If the desired testing and/or processing is not completed, then the rack 100 may re-circulate one or more times. As shown, each rack 100 does not need to be full. The system 620, as shown, includes multiple turntables 652A, 652B of the type previously described with reference to FIGS. 5A-5D to move the racks 100 at the corners. Additional turntables may be provided, such as turntable 652C, which operates as discussed previously, but may not include indentations. Turntable 652C simply aids the rack 100 in turning the corner. The inflow and outflow lanes 660, 662 may be loaded with racks 100 manually or by automation. Optionally, the inflow and outflow lanes 660, 662 may be coupled to a larger conveyor system (not shown) and several systems like system 600 may be linked, or the system 600 may be linked, to a primary track or track loop.

Figure 7:
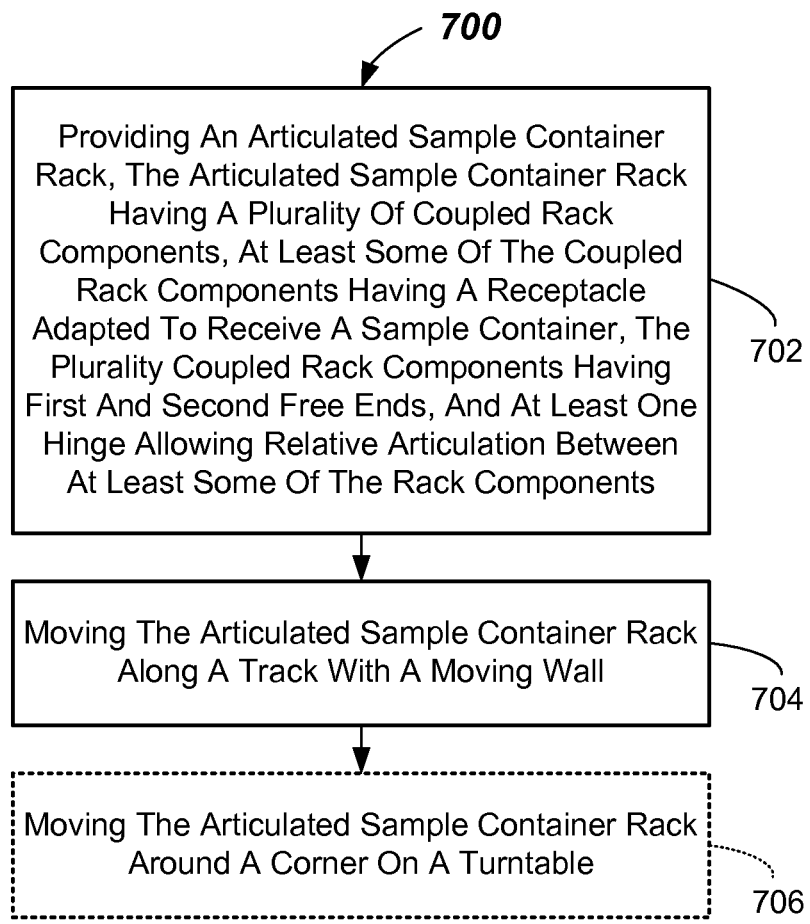
FIG. 7 is a flowchart illustrating methods according to embodiments.

Referring now to FIG. 7, a broad method of operating a conveyor system (e.g., system 120, 520, or 620) according to one or more embodiments is illustrated. The method 700 includes, in 702, providing an articulated sample container rack (e.g., 100, 200, 300, or 400), the articulated sample container rack having a plurality of coupled rack components (e.g., 102, 202, 302, or 402), at least some of the coupled rack components having a receptacle (e.g., 104, 204, 304, or 404) adapted to receive a sample container (e.g., 106), the plurality of coupled rack components having first and second free ends, and at least one hinge (e.g., 112, 412) allowing relative articulation between at least some of the rack components. In 704, the articulated sample container rack is moved along a track (e.g., tracks 540, 542, 640, or 642) with a moveable wall (e.g., 124, 524). Moveable wall may include cleats 124C.

As discussed above, the motion of the sample rack 100 along the track in some embodiments may be provided by the moveable wall (e.g., 124, 524) in conjunction with a secondary moveable wall (e.g., 126, 526). Other systems may include moveable wall (e.g., 124) and a stationary wall (e.g., 134). In some embodiments, the moveable wall (e.g., moveable wall 124) and a secondary moveable wall or moveable member (e.g., moveable member 132) may be moved at different rates to spin at least some of the rack components (e.g., rack components 102). In some embodiments, a turntable (e.g., turntable 552, 652A, 652B) may be provided and, as shown in 706, the articulated sample container rack (e.g., 100, 200, 300, or 400) may be moved around a track corner on a turntable (e.g., turntable 552, 652A, or 652B). In some embodiments, the turntable may be provided and the moveable wall (e.g., moveable wall 124) with cleats (e.g., cleats 124C) may disengage the articulated sample container rack (e.g., 100, 200, 300, or 400) in a track corner.

From the foregoing, it should be apparent that novel sample container rack apparatus, conveyor systems adapted to convey sample container racks, and methods of operating conveyor systems are provided. While the invention is susceptible to various modifications and alternative forms, specific system embodiments and methods thereof have been shown by way of example in the drawings and are described in detail herein. It should be understood, however, that it is not intended to limit the invention to the particular apparatus, systems or methods disclosed but, to the contrary, the intention is to cover all modifications, equivalents, and alternatives falling within the scope of the invention.

What is claimed is:

1. An articulated sample container rack apparatus, comprising:
a plurality of coupled rack components, at least some of the coupled rack components having a receptacle configured and adapted to receive a sample container, the receptacle including a bottom, the plurality of coupled rack components having first and second free ends, and at least one hinge allowing relative rotation between at least some of the rack components, wherein the at least one hinge comprises a first part and a second part, and at least one of the coupled rack components comprises or is coupled to both the first part and the second part each fixedly positioned relative to each other without an intervening third part connected between and to the first part and the second part to form the at least one hinge.

2. The rack apparatus of claim 1, wherein a number of rack components between the first and second free ends in the sample rack apparatus is 15 or less.

3. The rack apparatus of claim 1, wherein a number of rack components between the first and second free ends in the sample rack apparatus is between 3 and about 10.

4. The rack apparatus of claim 1, wherein a number of rack components in the sample rack apparatus is between 3 and 7.

5. The rack apparatus of claim 1, wherein each of the rack components are individually rotatable by 360 degrees or more.

6. The rack apparatus of claim 1, wherein at least one of the at least one hinge is offset from a location of the receptacles.

7. The rack apparatus of claim 1, wherein the at least one hinge is substantially aligned with a location of a receptacle.

8. The rack apparatus of claim 1, wherein the at least one hinge comprises:
a plurality of links coupled to each of the rack components.

9. The rack apparatus of claim 8, comprising:
end links and spacers coupled to each end rack component of the rack components.

10. The rack apparatus of claim 8, comprising:
retainers coupled to each of the rack components, the retainers coupled to the rack components to restrain vertical motion of the plurality of links relative to the rack components, yet allow rotation of the rack components relative to the plurality of links.

11. The rack apparatus of claim 1, comprising:
a component-to-component articulation angle capability of at least 15 degrees.

12. An articulated sample container rack apparatus, comprising:
a plurality of rack components having a total number of between 3 and about 10, at least some of the rack components having a receptacle adapted to receive a sample container, wherein the receptacle includes a sidewall and a bottom;
link sets connected to the rack components at first and second vertically-spaced locations, wherein a first link of a link set at the first vertically-spaced location is fixedly positioned relative to a second link of the link set at the second vertically-spaced location without having an intervening link part connected between and to the first link and the second link; and
retainers coupled to each of the rack components to restrain vertical motion of the link sets relative to the rack components, and yet allow rotation of the rack components relative to the link sets.

13. A sample container rack conveyor system, comprising:
a track formed between a first wall and a second wall, at least one of the walls comprising a moveable wall having cleats extending into the track; and
an articulated sample container rack adapted to be moved along the track by the moveable wall, the articulated sample container rack having a plurality of coupled rack components, at least some of the coupled rack components having a receptacle adapted to receive a sample container, the plurality of coupled rack components having first and second free ends, and at least one hinge allowing articulation between at least some of the coupled rack components, wherein the at least one hinge comprises a first part and a second part, and at least one of the coupled rack components comprises or is coupled to both the first part and the second part each fixedly positioned relative to each other without an intervening third part connected between and to the first part and the second part to form the at least one hinge.

14. The sample container rack conveyor system of claim 13, wherein the moveable wall comprises an endless belt and the cleats are formed along the endless belt.

15. The sample container rack conveyor system of claim 14, wherein the cleats engage spaces between adjacent rack components along the moveable wall.

16. The sample container rack conveyor system of claim 15, further comprising a track corner wherein the cleats disengage the spaces between the rack components in the track corner.

17. The sample container rack conveyor system of claim 13, further comprising a turntable configured to engage at least some of the rack components at a track corner.

18. The sample container rack conveyor system of claim 17, wherein the turntable comprises indentations adapted to receive a bottom of at least some of the rack components.

19. The sample container rack conveyor system of claim 13, wherein the track comprises a stationary floor.

20. A method of conveying a sample rack, comprising:
providing an articulated sample container rack, the articulated sample container rack having a plurality of coupled rack components, at least some of the coupled rack components having a receptacle adapted to receive a sample container, the plurality of coupled rack components having first and second free ends, and at least one hinge allowing articulation between at least some of the rack components, wherein the at least one hinge comprises a first part and a second part, and at least one of the coupled rack components comprises or is coupled to both the first part and the second part each fixedly positioned relative to each other without an intervening third part connected between and to the first part and the second part to form the at least one hinge; and
moving the flexible sample container rack along a track with a moveable wall.

21. The method of claim 20, further comprising:
moving the articulated sample container rack along the track with the moveable wall and a secondary moveable wall.

22. The method of claim 20, further comprising:
moving the moveable wall and a secondary moveable wall or moveable member at different rates to spin at least some of the rack components.

23. The method of claim 20, further comprising:
providing the moveable wall with cleats that disengage the articulated sample container rack in a track corner.

24. The method of claim 20, further comprising:
moving the articulated sample container rack around a track corner on a turntable.

* * * * *